United States Patent [19]

Salvador Palacios et al.

[11] Patent Number: 5,400,642
[45] Date of Patent: Mar. 28, 1995

[54] PROCEDURE AND APPARATUS FOR PROGRAMMED THERMAL DESORPTION

[75] Inventors: Francisco Salvador Palacios; Maria D. Merchan Moreno, both of Salamanca, Spain

[73] Assignee: Universidad de Salamanca, Spain

[21] Appl. No.: 89,336

[22] Filed: Jul. 12, 1993

[30] Foreign Application Priority Data

Jul. 10, 1992 [ES] Spain .................................. 9201729

[51] Int. Cl.$^6$ ...................... G01N 30/00; G01N 25/00
[52] U.S. Cl. ........................................ 73/23.2; 374/45
[58] Field of Search ............................ 374/45; 73/23.2

[56] References Cited

U.S. PATENT DOCUMENTS

| | | | |
|---|---|---|---|
| 4,994,158 | 2/1991 | Kiimalainen et al. | 73/23.2 |
| 5,131,260 | 7/1992 | Brand et al. | 73/23.2 |
| 5,268,302 | 12/1993 | Rounbehler et al. | 73/23.2 |

FOREIGN PATENT DOCUMENTS

| | | | |
|---|---|---|---|
| 0213031 | 3/1987 | European Pat. Off. | 73/23.2 |
| 0114761 | 6/1985 | Japan | 73/23.2 |
| 3144360 | 6/1991 | Japan | 73/23.2 |
| 4-04343057 | 11/1992 | Japan | 73/23.2 |
| 1488535 | 6/1989 | U.S.S.R. | 73/23.2 |

*Primary Examiner*—Diego F. F. Gutierrez
*Attorney, Agent, or Firm*—Wigman, Cohen, Leitner & Myers

[57] ABSTRACT

Method and apparatus for thermal desorption wherein a carrier liquid is circulated around a desorption chamber when a sample to be desorbed in heated, whereby the desorbed substance is dissolved into the carrier liquid for transport to a region where the substance is analyzed. The carrier liquid circulation is performed at high pressure sufficient to maintain the carrier liquid in the liquid phase during heating of the sample.

7 Claims, 1 Drawing Sheet

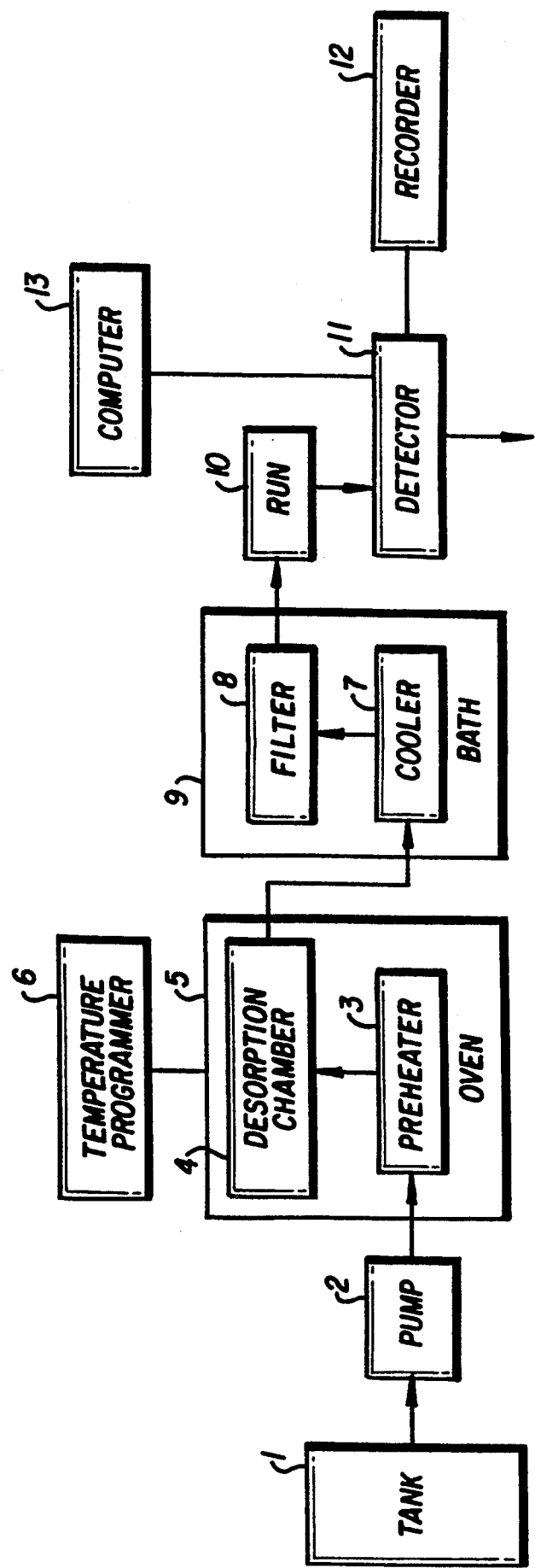

PROCEDURE AND APPARATUS FOR PROGRAMMED THERMAL DESORPTION

FIELD OF THE INVENTION

The present invention relates to a programmed thermal desorption (PTD) procedure as well as to a simple and easy to assemble piece of apparatus for carrying out said procedure.

BACKGROUND OF THE INVENTION

Thermo-programmed desorption is a widely used analysis technique in which the gas molecules absorbed by a solid surface are extracted by thermal heating. Since its beginnings in the 1940's it has only been applied to the desorption of gases. In 1990 IUPAC (International Union of Pure and Applied Chemistry) described it as an experimental technique for characterizing surfaces (Pure and Applied Chemistry vol 62, No. 12 pp 2297–2322, 1990) and they too make reference only to the desorption of gases. The present invention can be considered as the first piece of equipment described for carrying out PTD analysis in solution, opening up the possibility of extending the technique to a great many areas of research.

In a typical thermo-programmed desorption experiment a small amount of solid containing an absorbed gas is introduced into a reactor arranged inside an oven. The reactor is heated, generally following a linear increase in temperature with time. As the temperature rises the absorbed gas desorbs. An inert gas, generally helium, flows through the reactor and carries the desorbed gas molecules towards a detector. Alternatively the molecules are drawn by a vacuum.

A small thermocouple inserted inside the reactor measures the temperature while the detector in contact with the current of carrier gas analyzes the concentration of the gas desorbed. The response of the detector is proportional to the rate of desorption. This rate increases with temperature, reaches a maximum value and returns to zero when the surface is completely empty.

The desorption spectrum (thermogram) is a recording of the concentration of the gas desorbed as a function of temperature. Normally the spectrum can exhibit more than one maximum (peak).

The number, shape and position of the peaks, as well as the area contained within the thermogram, hold a great deal of information about the gas, the surface and the interaction between the two.

The thermo-desorption technique has its origins in the 1930's when URBACH, in is experiments on luminescence, observed the escape velocity of electrons from a continuously heated material. However, the application of this idea to the study of the interaction between gases and solids took place somewhat later.

The first work which refers to desorption itself was carried out by APKER and is described in his studies published in 1948 about the existing methods of measuring low pressures. These studies describe the difficulty in using ionization manometers as a result of the surface contamination of the filament by the absorption of gases, but show, nevertheless, that when subjected to abrupt heating, flash, there was a sudden increase in pressure due to the desorption of said gases.

In 1953 in the Bell Telephone laboratories (Murray, N.J.) HAGSTRUM designed and built several pieces of apparatus for studying the extraction of electrons from metal surfaces by bombardment with positive ions. These experiments show the importance of working with surfaces which are atomically clean. One indication of this contamination was the increase in pressure which took place when said surfaces were heated quickly to high temperature 1750 K.(Mo) or 2200 K. (W). Furthermore he observed that this increase was not uniform with temperature but could have maximum values.

In the same laboratories it was shown that the rate of gas desorption is dependant on temperature. The experiment was carried out in a vacuum system where an auxiliary filament of W or Mo was heated using a continuous current. An electronic circuit was designed to display the increase in pressure against the temperature on an oscilloscope screen. In this way the first desorption thermogram was obtained, i.e. the first representation of a variable related to the amount desorbed against temperature.

From this date on flash desorption began to develop widely, the heating process varying between 10 and 1200 K./s. In general, the equipment and procedures used were very similar. The solid under investigation was immersed in a gas connected to a vacuum system in which was located a device able to produce rapid heating. The amount of gas desorbed from the sample during the heating process could be determined by the increase in pressure inside the system, generally by means of an ionization manometer. By passing a current of gas to be absorbed by the surface after the flash, the equipment was once again ready for carrying out another desorption experiment.

Many studios have been carried out using the flash desorption equipment of the type described above. The first experiments concentrated on studying the absorption states of diatomic gases by W, while at the same time the theory required for the quantitative analysis of the experiments was developed. Later on said experiments dealt with the phenomena of interaction and interchange between gases absorbed by a surface. By 1963, the flash desorption technique had been more or less perfected. Among the many studies examined, it is worth mentioning the one carried out by AMENO-MIYA and CVETANOVIC regarding the interaction of ethylene with a surface of aluminium oxide. The apparatus was fitted with a controller, which enabled various linear rates of heating to be set, and a thermal conductivity thermistor for detecting the ethylene desorbed and carried along by a current of helium. Since the surface was non-metallic the rates of heating were much lower, between 0.5 and 40 K./min. The recorded desorption rate increased with temperature and later decreased as the absorbed gas was used up, tracing a peak. At the same time the temperature of the system was picked up by another recorder connected to the thermocouple.

From the experimental point of view the need to determine partial pressures in the gas phase of a system stimulated the use of various types of mass spectrometer, this kind of detector finding a clear application in the study of isotopic surface interchange reactions as well as for the study of the decomposition of substances absorbed by surfaces.

Another contribution in the field of thermo-desorption which is worthy of mention is that of CZAN-DERNA which deals with following the desorption process by direct weight using a microbalance. In this way it is possible to obtain a more direct measurement and work at high pressures. The studies of FARNETH are along the same lines and deal with the mechanism of oxidation of alcohols on $MoO_3$ where the desorption process was studied simultaneously by means of a balance and a mass spectrometer.

More recently the technique of programmed temperature desorption found an important application in the study of catalytic process. It was of course necessary to modify somewhat the previously described equipment as well as the process, due principally to the porous structure of the catalytic materials as opposed to the relatively uniform surface of the metallic materials which had previously been used.

Of the first work carried out it is worth mentioning that of CVETANOVIC and AMENOMIVA.

Their first study involves the modifications which have to be made to the flash desorption equipment. An oven was used to increase the temperature of the catalyst and an inert gas, helium, was used to carry the sample desorbed which was then analyzed by a chromatograph. The rates of heating were much lower, between 10 and 30 K./min such that the system remained close to a position of equilibrium between absorption and desorption.

Once the equipment had been modified the authors in their subsequent work moved on to the study of different catalytic systems: butene/aluminium, propylene/aluminium, ethylene/aluminium.

Later on slight modifications were introduced, relating principally to the means of detecting the species desorbed. This is the case for the equipment designed and perfected by MENON which uses a chromatograph as a detector in the study of n-pentane on Pt-$Al_2O_3$, the same as ANDERSON in his work on the desorption of hydrogen from the catalysts Pt and Au. Another means of detection is described in the work by TOPSOE which was to study the desorption of ammonium and pyridine from zeolites. In both cases infrared spectroscopy was used as the identification technique. The rate of heating varied between 5 and 40 K./min.

A more sophisticated modification was made by the investigators LATZEL and KAES who built a piece of apparatus in which the sample desorbed was drawn along by vacuum and which could function automatically. Both the oven and the type of heating were regulated by a computer which also controlled the mass spectrometer used as a detector and at the same time collected and stored all the data such as m/e, intensities, time, temperature, etc.

By the beginning of the 1980's the experimental equipment had already been more or less perfected. There have therefore been very few modifications since that time and work on thermo-desorption basically describes the results obtained or the theoretical considerations concerning the technique. A typical diagram of the apparatus from this period is included in the study by FALCONER.

Before concluding, there are two further issues worth mentioning: one is the changes in the rate of heating, and the other is the increase in complexity of the surfaces to be studied.

At first, the heating processes involved in flash desorption were very abrupt and poorly controlled, varying between 10 and 1200 K./s. As the equipment was perfected, this rate was reduced accordingly. For example, RIGBY worked with rates of heating between 5 and 32 K./s and years later AMENOMIYA and CVETANOVIC managed to work with rates of between 0.5 and 40 K./min. This reduction lead to the modification of the temperature detection system, the sensitivity of the thermocouples being insufficient, and enabled the problem of temperature gradients set up in the absorbent to be solved.

It is also worth mentioning the introduction of non-linear heating programmes such as those in which temperature and time vary reciprocally (hyperbolic heating). Hyperbolic heating implies greater complexity from the experimental point of view, but at the same time can improve the resolution of the thermogram and simplify the processing of the equations.

In 1962 REDHEAD published his work concerning the theoretical aspects of determining the activation energy, using the rates and orders of reaction for both types of heating, linear and hyperbolic, to make a comparative study.

In more recent years, studies on the thermo-programmed desorption of ammonium absorbed by zeolites using hyperbolic heating have shown that the kinetic parameters obtained with this procedure are more accurate than those obtained with linear heating and avoid the fairly frequent drawback of the sometimes observed dependence of these parameters on the rate of heating.

With regard to the surfaces studied the technique has undergone a long evolution. Initially, as has already been mentioned, the aim was to eliminate the absorbed contaminants absorbed by the filaments of ionization manometers. However, within a short time interest was centered instead on the absorption of these gases by metal surfaces and there are a great many studies concerning the absorption of nitrogen, hydrogen and carbon monoxide by metals, in most cases W. The reason for this continued interest is the direct relation to catalysis.

Later on the technique was applied to the study of more complex surface phenomena such as the desorption of the decomposed species from the surface, or those formed by catalytic effects. This is the case of the desorption of some organic compounds (ethane, methane, benzene) absorbed by metal surfaces such as W, Tr or Pt.

Once the necessary modifications in the equipment had been achieved and the application of the technique had been extended to the study of catalytic effects, work broadened further to cover porous catalysts. It is therefore worth mentioning the study of the absorption/desorption of hydrocarbons and alcohols by catalysts such as aluminium, carbon, silica gel, magnesium oxide, etc.

In recent years programmed desorption has also been used to characterize supported metals. The technique is now widely used for both porous and metal catalysts, or for metal oxide catalysts, and constitutes a valuable tool for the study of absorption/desorption surface phenomena as well as catalysis. Finally and as has already been shown, the application of this technique has only been carried out in the gas phase but never in the condensed phase. This could be due perhaps to the difficulty in reaching the required temperatures for desorption under these conditions, or to the scarcity of work and little development in the research into desorption in solution. The equipment designed therefore widens the field of thermo-programmed desorption.

SUMMARY OF THE INVENTION

The object of the present invention is a procedure for programmed thermal desorption based on the use of a liquid which can dissolve the substance desorbed and carry it along in this state for analysis.

A further object of the invention is a piece of apparatus for carrying out said procedure of programmed thermal desorption in solution, said apparatus being of simple construction, relatively reduced in cost and easy to handle compared with the equipment used for the thermo-programmed desorption of gases.

As in the case of the traditional processes, the procedure of the invention comprises the heating of the sample to be desorbed inside a chamber and the carrying of the substance desorbed to a region where it is analyzed, said process being characterized in that it uses a liquid which can dissolve the substance desorbed. The liquid is made to circulate around the desorption chamber during the heating phase. The liquid circulates around the heating chamber at high pressure, high enough to keep it in the liquid state during the heating period, such that desorption takes place while the carrier liquid is kept in a liquid phase. The substance desorbed is carried along in the dissolved state to a region where it is analyzed.

As it leaves the desorption chamber the carrier liquid in which the desorbed substance is dissolved is subjected to a partial cooling process before reaching the region where it is to be analyzed.

The apparatus required to carry out this procedure comprises a desorption chamber, means of heating said chamber and a detector in which the analysis of the desorbed substance takes place. According to the invention, the apparatus further includes means of supplying the desorption chamber with a liquid under pressure for carrying along the substance desorbed, means of heating the carrier liquid before it enters the desorption chamber, means of maintaining the carrier liquid at high pressure, at least while it circulates around the desorption chamber, and means of partially cooling the carrier liquid, said cooling means being situated between the desorption chamber and the detector for analyzing the desorbed substance.

BRIEF DESCRIPTION OF THE DRAWING

All characteristics of the invention, as described in the claims, are disclosed below in greater detail with the help of an accompanying drawing which represents schematically a non-limiting example of the apparatus required for carrying out the procedure of the invention.

DETAILED DESCRIPTION OF THE INVENTION

The accompanying drawing shows an example of the apparatus required for programmed thermal desorption in solution, said apparatus comprising a tank 1 for storing the carrier liquid, a high pressure pump 2 which forces the carrier liquid over a pre-heater 3 and the desorption chamber 4. The pre-heater 3 consists of a coil which, together with the desorption chamber 4, is located inside an oven 5 provided with a temperature programmer 6. Following the desorption chamber, and outside the oven 5, is a cooler 7 which may take the form of a coil and which is submerged in a thermostatic bath 9. A protective filter 8 is provided after the cooler 7, and outside the bath 9 is a run 10 which includes a reduction in cross-sectional area and which may consist, for example, of a capillary tube or an adjustable valve. After this run 10 is the detector 11 where the analysis of the desorbed substance takes place. The data provided may be collected and displayed graphically on a recorder 12 and processed by a computer 13. The novel part of the apparatus is the region which lies between the pump 2 and the run 10 which comprises the reduction in cross-sectional area, said region constituting the region of high pressure, the fundamental idea of the procedure being to maintain the desorption chamber 4 at high pressure during the entire heating process in order that desorption while the carrier liquid is kept in a liquid phase. These conditions of pressure may be achieved by increasing the loss of load of the carrier liquid after it has passed through the desorption chamber, or by using a capillary tube 10 or alternatively by means of an adjustable valve, as has already been indicated. Nevertheless, the pressure is also controlled and depends on the rate of flow which is chosen for the carrier liquid.

The carrier liquid, stored in the tank 1, is forced around the apparatus by the high pressure pump via the pre-heater 3 which terminates at the desorption chamber 4, said chamber being provided with filtration discs to prevent particles of the support material from being carried along.

The chamber 4 and the pre-heater 3 are placed inside the oven 5 which is provided with or connected to a temperature programmer 6 with which different rates of heating can be achieved.

The cooler 7 may also take the form of a coil and is suspended inside the thermal bath 9. The substance desorbed and swept along by the carrier liquid is cooled and kept at a constant temperature by the cooler 7 before it arrives at the detector 11. The purpose of the filter 8 is to prevent the passage of any solid particles which may be accidentally swept along by the liquid, thereby protecting the capillary tube 10.

The signal from the detector is displayed graphically along with the temperature (thermogram) on the graphical recorder 12 and may also be processed by computer.

The volume of the system as a whole should be small to minimize the amount of carrier liquid used up and so that the substance desorbed arrives immediately at the detector 11 for analysis.

The pump 2 used for supplying the liquid under pressure should enable high pressures to be obtained. The upper limit is determined by the critical pressure of the carrier liquid. Furthermore, the pump should be able to provide a wide range of flow rates which must be both accurate and constant. The pump, as well as the conduits and other components, must of course be inert to the various solvents which are to be used as carrier liquids.

The pre-heater 3 must be inert to the carrier liquid and able to withstand high pressures and temperatures, being built of a material with high thermal conductivity so that while it is inside the pre-heater the carrier liquid reaches the temperature of the oven. A simple pre-heater could consist of a coil formed by a long tube made of stainless steel or of steel with an inner lining of glass.

The desorption chamber 4 must also be inert to the carrier liquid and to the species desorbed, be able to withstand high temperatures and pressures and have a high thermal conductivity. At the same time it must able to retain the solid sample and allow the carrier liquid to circulate freely. The chamber 4 must be easy to open in order to fit the sample and its volume should be as small as possible, just enough to contain said sample, with a small cross-sectional area so that the carrier liquid flows at high speed, carrying along the desorbed molecules and preventing them from being re-absorbed. One simple design for the desorption chamber could take the form of a small, stainless steel cylinder with an internal diameter of a few millimeters, conically closed and provided with filtration plates at each end to prevent the passage of solid particles from the support but allowing the passage of the carrier liquid.

The oven 5 may have any shape and size, and conveniently is provided with a forced convection device so that no local temperature gradients are created and to rapidly achieve a uniform temperature as set by the programmer 6, facilitating and increasing the transmission of heat through the pre-heater 3 and the desorption chamber 4. It is also advisable that it be provided with a cooling device, for example a coil connected to a cryostat, so that the oven can be rapidly cooled after each experiment and furthermore to be able to start the desorption process a low temperatures, which is sometimes convenient.

Finally, the oven 5 should be provided with, or be easily connected to, a simple and accurate programmer 6, since in solution small variations in the rate of heating are enough to produce substantial changes in the rate of desorption.

Like the other components in the circuit, the cooler 7 must be inert to the carrier liquid and to the substances desorbed. Furthermore, it must be able to withstand high temperatures and pressures and have a high thermal conductivity so that it can quickly cool the current of carrier liquid. This part of the equipment could consist simply of a long, fine coil of steel, as shown in the drawing, with an inner lining of glass or another inert material, submerged in the thermostatic bath 9.

If the reduction in cross-sectional area, for maintaining the region of high pressure, consists of a capillary tube 10, said tube consists of a material which is inert to the carrier liquid and to the substances desorbed. The tube must also be able to withstand high pressures and its length and cross-sectional area should be such that they provide the necessary pressure inside the desorption chamber 4 and inside the cooling coil 7 so that the system remains in the liquid phase. As has already been mentioned, the capillary tube 10 could be replaced by an adjustable valve to achieve the same purpose.

The detector 11, where the analysis of the desorbed substance takes place, can be of any known type which can measure directly or indirectly the concentration of the desorbed substance in the flow of the carrier liquid. Some detectors which may be of good general use are: spectrophotometers (ultraviolet, visible, infrared, fluorescent, etc.), mass spectrometers, conductivity detectors, electrochemical detectors, etc.

Both the process and the apparatus of the invention can be of great use in any research or laboratory or industry involving work with solid surfaces and processes of absorption and catalysis, either as research apparatus or as a piece of equipment for controlling a particular process. Thus, for example, it could be used for controlling the dying of fibres, for the control and recovery of absorbents and catalysts, for controlling the elimination of contaminants by means of absorbents, etc.

We claim:

1. A thermal desorption procedure comprising the heating of a sample to be desorbed and the carrying of a substance desorbed from the sample to a region where it is analyzed, characterized in that a carrier liquid is made to circulate around a desorption chamber during the heating of the sample, said carrier liquid being able to dissolve the substance desorbed and said carrier liquid circulation taking place at high pressure, enough to maintain the carrier liquid in a liquid phase during the heating period of the desorption procedure, the substance desorbed being swept along in a dissolved state to the region where it is to be analyzed.

2. A procedure according to claim 1 characterized in that once the carrier liquid in which the desorbed substance is dissolved is outside the desorption chamber, the carrier liquid is subjected to a partial cooling process before it reaches the region where it is to be analyzed.

3. An apparatus for carrying out a process of thermal desorption comprising a desortion chamber throughout which a carrier liquid is made to circulate, means for heating the desorption chamber and a detector where the analysis of a desorbed substance takes place, means for supplying a carrier liquid under pressure to the desorption chamber for carrying the desorbed substance along, means for heating the carrier liquid before it enters the desorption chamber, means for maintaining the high pressure of the carrier liquid at least while it is circulating inside the desorption chamber, and means for partially cooling the carrier liquid, said partial cooling means being situated between the desorption chamber and the detector for analyzing the species desorbed.

4. The apparatus according to claim 3 wherein the means for supplying the carrier liquid under pressure comprises a high pressure pump to which the carrier liquid is supplied from a tank containing the carrier liquid.

5. The apparatus according to claim 3 wherein the means for heating the carrier liquid comprises an oven which houses the desorption chamber and part of the conduit in which the carrier liquid circulates under pressure before reaching said chamber, this part of the conduit being configured in the form of a coil.

6. The apparatus according to claim 3 wherein the means for maintaining the high pressure of the carrier liquid comprises a reduction in cross-sectional area produced in a circulation path followed by the carrier liquid under pressure, said reduction being situated between the desorption chamber and the detector for analyzing the substance desorbed, preferably upstream of the means of partially cooling the carrier liquid, the circulation path including a protective filter situated before said reduction in cross-sectional area.

7. The apparatus according to claim 3 wherein the means for partially cooling the carrier liquid comprises a thermostatic bath through which passes a run of the conduit in which the carrier liquid circulates under pressure with the desorbed substance, said run being configured in the form of a coil.

* * * * *